United States Patent
Timken et al.

(10) Patent No.: US 8,524,623 B2
(45) Date of Patent: Sep. 3, 2013

(54) ELECTROCHEMICAL REMOVAL OF CONJUNCT POLYMERS FROM CHLOROALUMINATE IONIC LIQUIDS

(75) Inventors: Hye-Kyung Timken, Albany, CA (US); Saleh Elomari, Fairfield, CA (US); Thomas V. Harris, Benicia, CA (US); James N. Ziemer, Martinez, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1040 days.

(21) Appl. No.: 12/437,508

(22) Filed: May 7, 2009

(65) Prior Publication Data

US 2010/0130804 A1   May 27, 2010

Related U.S. Application Data

(60) Provisional application No. 61/118,215, filed on Nov. 26, 2008.

(51) Int. Cl.
  *C07C 2/58* (2006.01)

(52) U.S. Cl.
  USPC ............ 502/22; 585/708; 585/711; 502/53; 502/29; 502/32; 502/155; 502/167; 502/150; 502/20; 502/25; 502/24; 208/15

(58) Field of Classification Search
  USPC ............ 585/711, 708; 502/53, 29, 32, 155, 502/167, 150, 5, 25, 20; 208/15
  See application file for complete search history.

(56) References Cited

U.S. PATENT DOCUMENTS

| 2,463,610 | A | * | 3/1949 | Glassmire et al. ............ 585/705 |
| 7,432,408 | B2 |  | 10/2008 | Timken et al. |
| 2006/0151335 | A1 |  | 7/2006 | Tian et al. |
| 2007/0142211 | A1 | * | 6/2007 | Elomari et al. ............... 502/29 |
| 2007/0142213 | A1 |  | 6/2007 | Elomari et al. |
| 2007/0142214 | A1 |  | 6/2007 | Elomari et al. |
| 2007/0142215 | A1 |  | 6/2007 | Harris et al. |
| 2007/0142216 | A1 |  | 6/2007 | Harris et al. |
| 2007/0142217 | A1 |  | 6/2007 | Elomari et al. |
| 2007/0142218 | A1 |  | 6/2007 | Harris et al. |
| 2007/0142676 | A1 |  | 6/2007 | Elomari et al. |
| 2007/0249485 | A1 | * | 10/2007 | Elomari et al. ............... 502/20 |
| 2007/0249486 | A1 |  | 10/2007 | Elomari et al. |
| 2008/0080370 | A1 |  | 4/2008 | Willey |
| 2008/0080378 | A1 |  | 4/2008 | Kim et al. |

OTHER PUBLICATIONS

A. Bogaerts et al. Spectrochimica Acta Part B 57 (2002) 609-658.*
Eisenberg et al. Ionic Mass Transfer and Concentration Polarization at Rotating Electrodes. Journal of the Electrochemical Society. Jun. 1954. vol. 101 No. 6, pp. 306-320.*
PCT/US2009/061026. PCT International Preliminary Report on Patentability, mailed Jun. 9, 2011.

* cited by examiner

*Primary Examiner* — In Suk Bullock
*Assistant Examiner* — Sharon Pregler
(74) *Attorney, Agent, or Firm* — Susan M. Abernathy; Steven H. Roth

(57) ABSTRACT

A process for regenerating a spent ionic liquid catalyst including (a) applying a voltage across one or more pairs of electrodes immersed in a spent ionic liquid catalyst comprising conjunct polymer-metal halide complexes to provide freed conjunct polymers and a regenerated ionic liquid catalyst; and (b) separating the freed conjunct polymers from the regenerated ionic liquid catalyst is described. An alkylation process incorporating the regeneration process is also described.

24 Claims, No Drawings

ELECTROCHEMICAL REMOVAL OF CONJUNCT POLYMERS FROM CHLOROALUMINATE IONIC LIQUIDS

This application claims the benefit of provisional Application No. 61/118,215, filed Nov. 26, 2008, herein incorporated in its entirety.

FIELD OF ART

The processes described herein relate to the removal of conjunct polymers from an ionic liquid catalyst. More particularly, the processes described herein involve the regeneration of an ionic liquid catalyst by the removal of conjunct polymers from the ionic liquid catalyst by employing an electrochemical technique.

BACKGROUND

An alkylation process, which is disclosed in U.S. Pat. No. 7,432,408 ("the '408 patent"), involves contacting isoparaffins, preferably isopentane, with olefins, preferably ethylene, in the presence of an ionic liquid catalyst to produce gasoline blending components. The contents of the '408 patent are incorporated by reference herein in its entirety.

An ionic liquid catalyst distinguishes this novel alkylation process from conventional processes that convert light paraffins and light olefins to more lucrative products such as the alkylation of isoparaffins with olefins and the polymerization of olefins. For example, two of the more extensively used processes to alkylate isobutane with $C_3$-$C_5$ olefins to make gasoline cuts with high octane numbers use sulfuric acid ($H_2SO_4$) and hydrofluoric acid (HF) catalysts.

As a result of use, ionic liquid catalysts can become deactivated, i.e. lose activity, and may eventually need to be replaced. Alkylation processes utilizing an ionic liquid catalyst can form by-products known as conjunct polymers. These conjunct polymers generally deactivate the ionic liquid catalyst by forming complexes with the ionic liquid catalyst. Conjunct polymers are highly unsaturated molecules and can complex the Lewis acid portion of the ionic liquid catalyst via their double bonds. For example, as aluminum trichloride in aluminum trichloride-containing ionic liquid catalysts becomes complexed with conjunct polymers, the activity of these ionic liquid catalysts becomes impaired or at least compromised. Conjunct polymers may also become chlorinated and through their chloro groups may interact with aluminum trichloride in aluminum trichloride-containing catalysts and therefore reduce the overall activity of these catalysts or lessen their effectiveness as catalysts for their intended purpose.

Deactivation of ionic liquid catalysts by conjunct polymers is not only problematic for alkylation chemistry, but also affects the economic feasibility of using ionic liquid catalysts as they are expensive to replace. Therefore, commercial exploitation of ionic liquid catalysts in alkylation is economically infeasible unless they can be efficiently regenerated and recycled.

A few methods for regenerating ionic liquid catalysts, which involve removing conjunct polymers from the catalysts, have been devised. These regeneration methods involve hydrogenation of the conjunct polymers, addition of a reagent capable of replacing the complexed conjunct polymers, and alkylation of the conjunct polymers.

Regeneration methods involving hydrogenation of the conjunct polymers are described in U.S. Patent Application Publication Nos. 2007/0142218 ("the '218 publication"), 2007/0142217 ("the '217 publication"), 2007/0142215 ("the '215 publication"), 2007/0142214 ("the '214 publication"), and 2007/0142213 ("the '213 publication"). The '218 publication is directed to a process for regenerating a used acidic ionic liquid catalyst comprising the steps of contacting the used ionic liquid catalyst and hydrogen with a homogeneous hydrogenation catalyst in a reaction zone under hydrogenation conditions for a time sufficient to increase the activity of the used catalyst. The '217 publication is directed to a process for regenerating a used acidic ionic liquid catalyst which has been deactivated by conjunct polymers comprising combining the used catalyst, a metal, and a Broensted acid which acts as a source of hydrogen in a reaction zone under hydrogenation conditions for a time sufficient to hydrogenate at least a portion of the conjunct polymer. The '215 publication relates to a process for regenerating a used acidic ionic liquid catalyst comprising the steps of contacting the used ionic liquid catalyst and hydrogen with a supported hydrogenation catalyst comprising a hydrogenation component on a support in a reaction zone under hydrogenation conditions for a time sufficient to increase the activity of the used catalyst. The '214 publication relates to a process for regenerating a used acidic ionic liquid catalyst which has been deactivated comprising the steps of contacting the used chloroaluminate ionic liquid catalyst and hydrogen with a metal hydrogenation catalyst in a reaction zone under hydrogenation conditions for a time sufficient to increase the activity of the ionic liquid catalyst. The '213 publication relates to a process for regenerating a used acidic catalyst which has been deactivated by conjunct polymers by removing the conjunct polymers so as to increase the activity of the catalyst. The '213 publication discusses hydrogenation as one method of removing the conjunct polymers.

Regeneration methods involving the addition of a reagent capable of replacing the complexed conjunct polymers are described in the '213 publication and U.S. Patent Application Publication No. 2007/0142211 ("the '211 publication"). As discussed above, the '213 publication relates to a process for regenerating a used acidic catalyst which has been deactivated by conjunct polymers by removing the conjunct polymers so as to increase the activity of the catalyst. The '213 publication discusses addition of a basic reagent as another method of removing the conjunct polymers. The '211 publication is directed to a process for regenerating a used ionic liquid catalyst comprising a cationic component and an anionic component, which catalyst has been deactivated by conjunct polymers complexed with the anionic component comprising the steps of adding a reagent which is capable of replacing the complexed conjunct polymer with the cationic component of the catalyst, said reagent being added in an amount sufficient to increase the activity of the used ionic liquid catalyst.

A regeneration method involving alkylation of the conjunct polymers is described in the '213 publication and U.S. Patent Application Publication No. 2007/0142216 ("the '216 publication"). As discussed above, the '213 publication relates to a process for regenerating a used acidic catalyst which has been deactivated by conjunct polymers by removing the conjunct polymers so as to increase the activity of the catalyst. The '213 publication discusses alkylation as yet another method of removing the conjunct polymers. The '216 publication relates to a process for regenerating a used acidic ionic liquid catalyst comprising contacting the used ionic liquid catalyst with an isoparaffin-containing stream and Broensted acid in a reaction zone under alkylation conditions for a time sufficient to increase the activity of the ionic liquid catalyst.

Additional methods of regenerating a used or spent acidic ionic liquid catalyst involve contacting the used catalyst with a regeneration metal in the presence or absence of hydrogen. Such methods are described in U.S. Patent Application Publication Nos. 2007/0249486 ("the '486 publication") and 2007/024985 ("the '485 publication"). The '486 publication relates to a process for regenerating a used acidic ionic liquid catalyst comprising contacting the used ionic liquid catalyst with at least one regeneration metal in a regeneration zone in the presence of added hydrogen under regeneration conditions for a time sufficient to increase the activity of the ionic liquid catalyst. The '485 publication relates to a process for regenerating a used acidic ionic liquid catalyst comprising contacting the used ionic liquid catalyst with at least one metal in a regeneration zone in the absence of added hydrogen under regeneration conditions for a time sufficient to increase the activity of the ionic liquid catalyst.

However, while effective, each of these methods suffers from certain shortcomings. Thus, to take advantage of the potential of ionic liquids as catalysts, particularly in alkylation reactions, the industry continues to search for an effective and efficient process for removing conjunct polymers from ionic liquid catalysts to thereby regenerate the ionic liquid catalysts. In general, the process should be simple and efficient enough to be used to remove conjunct polymers from an ionic liquid catalyst quickly and effectively.

SUMMARY

Disclosed herein is a process for regenerating a spent ionic liquid catalyst, comprising: (a) applying a voltage across one or more electrode pairs immersed in a spent ionic liquid catalyst comprising conjunct polymer-metal halide complexes to provide freed conjunct polymers and a regenerated ionic liquid catalyst; and (b) separating the freed conjunct polymers from the regenerated ionic liquid catalyst.

Further disclosed herein is an alkylation process incorporating the process for regenerating a spent ionic liquid catalyst. The alkylation process comprises: (a) reacting isoparaffins with olefins in the presence of an ionic liquid catalyst comprising a metal halide to provide a spent ionic liquid catalyst comprising conjunct polymer-metal halide complexes and a hydrocarbon product; (b) applying a voltage across one or more electrode pairs immersed in the spent ionic liquid catalyst to provide freed conjunct polymers and regenerated ionic liquid catalyst; (c) separating the freed conjunct polymers from the regenerated ionic liquid catalyst; and (d) recycling the regenerated ionic liquid catalyst to the reaction step (a).

Among other factors, the processes as disclosed herein are simpler than existing regeneration processes and require simpler equipment than existing regeneration processes. The present processes do not require a chemical reagent to displace the conjunct polymers. The use of chemical reagents can form by-products, which accumulate in the catalyst phase and must be removed from the catalyst phase. For example, regenerating an ionic liquid catalyst with a metal can produce by-product metal halides, which accumulate in the catalyst phase and must be removed from the catalyst phase. Accordingly, the present processes do not require additional equipment and processes associated with by-product handling and removal. The present processes also do not require equipment and reagents associated with hydrogenation of conjunct polymers or alkylation of conjunct polymers.

DETAILED DESCRIPTION

Process for Regenerating a Spent Ionic Liquid Catalyst

Disclosed herein is a process for regenerating a spent ionic liquid catalyst. As used herein the term "spent ionic liquid catalyst" refers to an ionic liquid catalyst that has been at least partially deactivated. The spent ionic liquid catalyst can be either partially deactivated or fully deactivated.

The spent ionic liquid catalyst becomes deactivated due to the formation of by-product conjunct polymers, which interact with metal halides in the ionic liquid catalyst and form conjunct polymer-metal halide complexes. Thus, the spent ionic liquid catalyst comprises conjunct polymer-metal halide complexes that deactivate the catalyst.

The present process for regenerating a spent ionic liquid catalyst involves applying a voltage across one or more electrode pairs immersed in a spent ionic liquid catalyst, which comprises conjunct polymer-metal halide complexes, to provide freed conjunct polymers and a regenerated ionic liquid catalyst. According to the process, the freed conjunct polymers can then be separated from the regenerated ionic liquid catalyst.

Without being bound by theory, the voltage application step is believed to have the following effects. Applying voltage across the one or more electrode pairs immersed in the spent ionic liquid catalyst electrochemically reduces at least a portion of the conjunct polymers of the conjunct polymer-metal halide complexes such that at least a portion of the conjunct polymers are no longer complexed with the metal halides of the ionic liquid catalyst. The electrochemical reduction of the conjunct polymers leads to the break-up of at least a portion of the conjunct polymer-metal halide complexes thereby freeing the conjunct polymers from the catalyst and providing freed conjunct polymers and regenerated ionic liquid catalyst. Accordingly, the electrochemical reduction eliminates at least a portion of the conjunct polymer-metal halide complexes. The freed conjunct polymers have limited solubility in the bulk phase of the regenerated ionic liquid catalyst and can then be removed from the regenerated ionic liquid catalyst, for example, by extraction with a suitable solvent.

As used herein, the term "regenerated ionic liquid catalyst" refers to ionic liquid catalyst that is either fully regenerated or partially regenerated. Fully regenerated ionic liquid catalyst is substantially free from conjunct polymer-metal halide complexes. Partially regenerated ionic liquid catalyst still includes conjunct polymer-metal halide complexes such that it is not substantially free from conjunct polymer-metal halide complexes.

The conjunct polymers can deactivate ionic liquid catalysts by forming complexes with or simply interacting with the ionic liquid catalyst. It is believed that complexes form because conjunct polymers, by virtue of their double bonds, form pi ($\pi$) complexes with or sigma ($\sigma$) bonds with the Lewis acid species, such as metal halides, in the ionic liquid catalyst. As an example, conjunct polymers can complex with $AlCl_3$, a Lewis acid present in chloroaluminate ionic liquid catalysts such as 1-butyl-pyridinium heptachloroaluminate. Conjunct polymers may complex $AlCl_3$ via their double bonds to make reversible pi-complexes. The pi-complexes may convert to irreversible sigma-complexes. Conjunct polymers with their cationic character may also complex chloroaluminate species resulting in more deactivating complexes.

As used herein, the term "conjunct polymer-metal halide complexes" refers to associations of molecules formed as the result of binding between or attractive forces between conjunct polymers and metal halides.

The term "conjunct polymer" as used herein refers to a polymeric compound that might bond to a cationic species of an ionic liquid catalyst by pi bonding or sigma bonding or other means, which results in the polymeric compound binding to the catalyst, so that it is not removable by simple hydrocarbon extraction.

The term conjunct polymer was first used by Pines and Ipatieff to distinguish these polymeric molecules from the usual polymers. Unlike typical polymer, conjunct polymers are polyunsaturated cyclic, polycyclic and acyclic molecules formed by concurrent acid-catalyzed reactions including, among others, polymerization, alkylation, cyclization, and hydride transfer reactions. Conjunct polymers consist of an unsaturated intricate network of molecules that may include one or a combination of 4-, 5-, 6- and 7-membered rings and some aromatic entities in their skeletons. Some examples of the likely polymeric species were reported by Miron et al. (*Journal of Chemical and Engineering Data*, 1963) and Pines (*Chem. Tech*, 1982), which documents are incorporated by reference in their entirety herein. These molecules contain double and conjugated bonds in intricate structures containing a combination of cyclic and acyclic skeletons.

In practice, conjunct polymers are also called "red oils" due to their color and "acid-soluble oils" due to their high uptake in the catalyst phase where saturated hydrocarbons and paraffinic products are usually immiscible.

According to the present process, any device known in the art that is capable of producing electric current between a pair of electrodes can apply voltage across the one or more electrode pairs immersed in the spent ionic liquid catalyst. In one embodiment, the voltage application step occurs by applying a voltage across a single pair of electrodes immersed in the spent ionic liquid catalyst.

Application of voltage of sufficient magnitude across the pair(s) of electrodes induces one of the electrodes in each pair to undergo oxidation and act as a sacrificial anode (positive electrode), while the other electrode in each pair acts as the cathode (negative electrode) and provides a surface where dissolved metal ions of the ionic liquid catalyst's metal halide can plate out as metal. During the present process, the metal of the sacrificial anode dissolves and reacts with uncomplexed halide ions in solution to form fresh metal halide. Similarly, dissolved metal ions of the ionic liquid catalyst's metal halide plate out as metal onto the cathode.

Without being bound by theory, it is believed that the conjunct polymer complexed metal halide (e.g. conjunct polymer complexed aluminum chloride) is easier to reduce than the uncomplexed metal halide cation (e.g. $Al_2O_7^{+1}$). As such, if the voltage applied to the one or more pairs of electrodes is not too great, the conjunct polymer complexed metal halide reacts preferentially at the cathode. Accordingly, reduction of the conjunct polymer complexed metal halide provides plated metal (e.g. aluminum metal) at the cathode, freed conjunct polymer, and halide anion. Such reaction removes ionic liquid catalyst from the solution. Dissolving metal at the anode introduces metal ions (e.g. $Al^{3+}$) back into the solution and these metal ions react with excess, free halide anions in the solution to form fresh metal halide species in the ionic liquid catalyst, which makes up for the metal halide species lost when metal ions plate out as metal onto the cathode.

Generally, the sacrificial anode is composed of the same metal as the metal of the ionic liquid's metal halide. The cathode can be comprised of an electrically conducting metal, polymer, or carbon compound (e.g. graphite or carbon paste). Accordingly, in one embodiment, a first electrode of each electrode pair is composed of aluminum metal and a second electrode of each electrode pair comprises an electrically conducting metal, polymer, or carbon compound.

For example, in one embodiment where the ionic liquid catalyst is a chloroaluminate ionic liquid catalyst, the sacrificial anode is composed of aluminum metal, while the cathode is composed of an electrically conducting metal, polymer, or carbon compound (e.g. graphite or carbon paste). As a voltage of, for example, 1.5 volts is applied across the electrode pairs, the aluminum metal of the sacrificial anode dissolves and reacts with uncomplexed chloride ions in solution to form fresh $AlCl_3$. Similarly, dissolved aluminum ions plate out as aluminum metal onto the cathode.

For greatest effectiveness, the electrodes of the electrode pair(s) should be spaced far enough apart to prevent the dissolved metal ions from the anode from immediately undergoing reduction to metal at the cathode prior to reaction with excess halide in the solution to form the metal halide in the ionic liquid catalyst.

The amount of applied voltage may vary. Furthermore, the applied voltage can be either held constant to produce a direct current or can be varied regularly in time to produce an alternating current whereby each of the electrodes in each electrode pair alternates between anode and cathode in time. Accordingly, any numerical references to voltage applied herein refer to the magnitude of the difference of electrical potential between the two electrodes of each electrode pair.

In one embodiment, the voltage applied is between about 1.5 volts and about 5 volts. For example, the voltage applied may be between about 2 volts and about 3 volts. In another embodiment, the voltage applied is between about 1 volt and about 3 volts. In a particular embodiment, the voltage application step (a) further comprises applying a potential to each electrode in each electrode pair that is alternated in time so that each electrode in each electrode pair functions for brief periods of time as a sacrificial anode and for other periods of time as a cathode and further wherein the voltage applied in step (a) is between about 1 volt and about 3 volts.

In one embodiment, the voltage applied provides a current in the spent ionic liquid catalyst having a current density between about 1 and about 200 milliamps/cm$^2$ electrode. In another embodiment, the voltage applied fluctuates in time to maintain a constant current density in the spent ionic liquid catalyst between about 1 and about 200 milliamps/cm$^2$ electrode.

The length of time that the voltage is applied may also vary. Generally, the length of time is longer for a greater degree of catalyst deactivation or for a lower applied potential difference (i.e. lower voltage applied). In one embodiment, the voltage is applied to a 0.1 liter ionic liquid solution with an electrode pair, each of which have surface areas between 1-3 cm$^2$, for between about 0.1 hours and about 5 hours. In another embodiment, the voltage is applied for between about 0.01, hours and about 12 hours. As the voltage is applied, the conjunct polymers in the conjunct polymer-metal halides complexes are reduced, which eliminates the complexes thereby freeing conjunct polymers and regenerating the ionic liquid catalyst. Thus, generally, the greater the degree of ionic liquid catalyst deactivation by conjunct polymers, the greater the total current needed to restore catalyst activity to a given activity and the longer the time needed to restore the catalyst activity to a given activity.

The effectiveness of the present process should improve by increasing the rate of liquid mass transport to the electrode surfaces. Such an increase in mass transport can be accomplished by any technique known in the art, for example, rapidly stirring the ionic liquid catalyst, pumping the ionic liquid catalyst through flow-through electrodes, or employing rotating disk electrodes, which induce convection currents in the ionic liquid catalyst towards the rotating electrode.

Any applicable separation technique known in the art can be used to separate the freed conjunct polymers from the regenerated ionic liquid catalyst. In one embodiment, the separation step can be selected from the group consisting of decantation, solvent extraction, and combinations thereof.

The freed conjunct polymers can be separated from the regenerated ionic liquid catalyst by decantation because the freed conjunct polymers form a hydrocarbon phase that is less polar and less dense than the ionic liquid catalyst phase. Accordingly, a decantation vessel may be used to withdraw the freed conjunct polymers from the top of the vessel and the ionic liquid catalyst phase from the bottom of the vessel.

Solvent extraction may also be used separate the freed conjunct polymers from the ionic liquid catalyst. Solvent extraction is well known and often practiced in the art. Solvent extraction of freed conjunct polymers is described in U.S. patent application Ser. No. 12/003,578, which is incorporated by reference in its entirety herein.

Hydrocarbon solvents successfully dissolve the conjunct polymers to remove them from the catalyst phase. Useful hydrocarbon solvents for the extraction include, but are not limited to, pentane, hexane, heptane, octane, decane and many other hydrocarbonaceous solvents. Solvents to be used can be low boiling solvents for ease of recovery and non-branched hydrocarbons to limit side reactions with the regenerated catalyst. Other examples of useful hydrocarbon solvents are n-butane, isobutane, and isopentane.

Solvent extraction may be successfully accomplished with a stirred extraction column or a packed column. High separation efficiency is achieved, with countercurrent flow through the columns working best. The packed column is simple, and with a sufficient flow rate good enough contact is realized to permit efficient and effective solvent extraction of the conjunct polymers. The extraction packings can be commonly available packings, e.g., structural metal packings, Raschig rings or Koch-Sulzer packings. The purpose of the packing is to increase surface area for contact and increase the efficiency of mixing. The stirred extraction column offers even improved contact between the two phases, and takes less solvent.

One or more hydrocarbon solvents may be added to the ionic liquid catalyst during or after the voltage application step. As the freed conjunct polymers are less polar than the ionic liquid catalyst, they will preferentially dissolve in, and be extracted by, the hydrocarbon solvent(s).

Conjunct polymers form during a variety of reactions in which ionic liquid catalysts are employed, for example, alkylation, polymerization, dimerization, oligomerization, acetylation, olefin metathesis, and copolymerization. The alkylation may be paraffin alkylation or aromatic alkylation. Conjunct polymers also form during olefin isomerization, desulfurization, and catalytic cracking. Additionally, conjunct polymers are by-products of many types of Friedel-Crafts reactions, which are reactions that fall within the broader category of electrophylic substitution, like alkylation and acylation. Accordingly, the present process is useful for regenerating a spent ionic liquid catalyst that has been used to catalyze any of these above-mentioned reactions.

In one embodiment, the spent ionic liquid catalyst has been used to catalyze a Friedel-Crafts reaction. This Friedel-Crafts reaction can be alkylation.

Regeneration restores the activity of the ionic liquid catalyst. Catalyst activity can be measured, for example, by titration. As discussed above, catalyst activity depends upon the acidity of the ionic liquid catalyst. Therefore, the amount of Lewis acid species (e.g. metal halide) that is not complexed with conjunct polymers provides an accurate measurement of catalyst activity. The amount of base necessary to titrate the protons released from hydrolyzing the ionic liquid catalyst may be used to calculate the acid content of the catalyst, which in turn provides an accurate measurement of catalyst activity. Titrating ionic liquid catalysts in order to ascertain their activity is discussed in a provisional U.S. Patent Application entitled "Monitoring of Ionic Liquid Catalyst Deactivation," which is being filed concurrently with the present application. This provisional application is incorporated by reference in its entirety herein.

The amount of base per gram of catalyst used to titrate the regenerated ionic liquid catalyst depends upon the composition of the ionic liquid catalyst (e.g. A/N molar ratio), the remaining conjunct polymer content, and the molecular weight of the catalyst. As an example, to regenerate a n-butylpyridinium chloroaluminate ionic liquid catalyst having an initial Al/N ratio between about 1.95 and about 2.0, voltage can be applied until the catalyst reaches an activity of between about 650 mg KOH/g ionic liquid and about 725 mg KOH/g ionic liquid. In one embodiment, voltage can be applied until the catalyst reaches an activity of between about 650 mg KOH/g ionic liquid and about 767 mg KOH/g ionic liquid. In another embodiment, voltage can be applied until the catalyst reaches an activity of between about 680 mg KOH/g catalyst and about 750 mg KOH/g catalyst.

Ionic Liquid Catalyst

Any type of ionic liquid catalyst may be utilized in the processes described herein. Ionic liquid catalysts are well known in the art.

As used herein, the term "ionic liquids" refers to liquids that are composed entirely of ions as a combination of cations and anions. The term "ionic liquids" includes low-temperature ionic liquids, which are generally organic salts with melting points under 100° C. and often even lower than room temperature.

Ionic liquids may be suitable, for example, for use as a catalyst and as a solvent in alkylation and polymerization reactions as well as in dimerization, oligomerization, acetylation, olefin metathesis, and copolymerization reactions.

One class of ionic liquids is fused salt compositions, which are molten at low temperature and are useful as catalysts, solvents, and electrolytes. Such compositions are mixtures of components, which are liquid at temperatures below the individual melting points of the components.

The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations, Anions include, but are not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many others. The most catalytically interesting ionic liquids for acid catalysis are those derived from ammonium halides and Lewis acids (such as $AlCl_3$, $TiCl_4$, $SnCl_4$, $FeCl_3$, etc.). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts.

The processes as described herein can employ a catalyst composition comprising at least one aluminum halide such as aluminum chloride, at least one quaternary ammonium halide and/or at least one amine halohydrate, and at least one cuprous compound. Such a catalyst composition and its preparation is disclosed in U.S. Pat. No. 5,750,455, which is incorporated by reference in its entirety herein.

Alternatively, the spent ionic liquid catalyst can be a chloroaluminate ionic liquid catalyst. For example, the chloroaluminate ionic liquid catalyst can be a pyridinium-based chloroaluminate ionic liquid catalyst, an imidazolium-based chloroaluminate ionic liquid catalyst, and mixtures thereof. These ionic liquids have been found to be much more effective in the alkylation of isopentane with ethylene than aliphatic ammonium chloroaluminate ionic liquid (such as tributyl-methyl-ammonium chloroaluminate).

The chloroaluminate ionic liquid catalyst can be: (1) a chloroaluminate ionic liquid catalyst comprising a hydrocarbyl substituted pyridinium halide of the general formula A below and aluminum trichloride or (2) a chloroaluminate ionic liquid catalyst comprising a hydrocarbyl substituted imidazolium halide of the general formula B below and aluminum trichloride. Such a chloroaluminate ionic liquid catalyst can be prepared by combining 1 molar equivalent hydrocarbyl substituted pyridinium halide or hydrocarbyl substituted imidazolium halide with 2 molar equivalents aluminum trichloride. The ionic liquid catalyst can also be (1) a chloroaluminate ionic liquid catalyst comprising an alkyl substituted pyridinium halide of the general formula A below and aluminum trichloride or (2) a chloroaluminate ionic liquid catalyst comprising an alkyl substituted imidazolium halide of the general formula B below and aluminum trichloride. Such a chloroaluminate ionic liquid catalyst can be prepared by combining 1 molar equivalent alkyl substituted pyridinium halide or alkyl substituted imidazolium halide with 2 molar equivalents of aluminum trichloride.

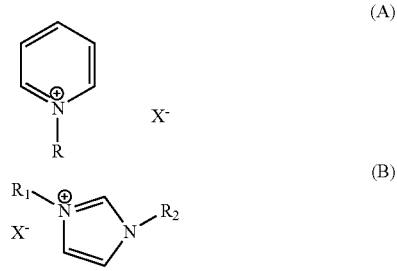

wherein R=H, methyl, ethyl, propyl, butyl, pentyl or hexyl group and X is a haloaluminate, and $R_1$ and $R_2$=H, methyl, ethyl, propyl, butyl, pentyl, or hexyl group and where $R_1$ and $R_2$ may or may not be the same. In one embodiment, the haloaluminate is a chloroaluminate. The spent ionic liquid catalyst can also be mixtures of these chloroaluminate ionic liquid catalysts.

Other examples of suitable chloroaluminate ionic liquid catalysts are 1-butyl-4-methyl-pyridinium chloroaluminate (BMP), 1-butyl-pyridinium chloroaluminate (BP), 1-butyl-3-methyl-imidazolium (BMIM), 1-H-pyridinium chloroaluminate (HP), and N-butylpyridinium chloroaluminate ($C_5H_5NC_4H_9Al_2Cl_7$), and mixtures thereof.

A metal halide may be employed as a co-catalyst to modify the catalyst activity and selectivity. Commonly used halides for such purposes include NaCl, LiCl, KCl, $BeCl_2$, $CaCl_2$, $BaCl_2$, $SiCl_2$, $MgCl_2$, $PbCl_2$, CuCl, $ZrCl_4$, and AgCl as published by Roebuck and Evering (Ind. Eng. Chem. Prod. Res. Develop., Vol. 9, 77, 1970), which is incorporated by reference in its entirety herein. Especially useful metal halides are CuCl, AgCl, $PbCl_2$, LiCl, and $ZrCl_4$. Another useful metal halide is $AlCl_3$.

HCl or any Broensted acid may be employed as an effective co-catalyst to enhance the activity of the catalyst by boosting the overall acidity of the ionic liquid-based catalyst. The use of such co-catalysts and ionic liquid catalysts that are useful in practicing the present processes are disclosed in U.S. Published Patent Application Nos. 2003/0060359 and 2004/0077914, the disclosures of which are herein incorporated by reference in their entirety. Other co-catalysts that may be used to enhance the catalytic activity of the ionic liquid catalyst include IVB metal compounds. In one embodiment, the co-catalysts include IVB metal halides such as $TiCl_3$, $TiCl_4$, $TiBr_3$, $TiBr_4$, $ZrCl_4$, $ZrBr_4$, $HfC_4$, and $HfBr_4$ as described by Hirschauer et al. in U.S. Pat. No. 6,028,024, which document is incorporated by reference in its entirety herein.

Alkylation Process

The presently disclosed process for regenerating a spent ionic liquid is particularly useful in an alkylation process. During alkylation, an ionic liquid catalyst may be used to facilitate reaction between isoparaffins and olefins. As used herein, the term "isoparaffin" means any branched-chain saturated hydrocarbon compound, i.e., a branched-chain alkane with a chemical formula of $C_nH_{2n+2}$. Examples of isoparaffins are isobutane and isopentane. The term "olefin," as used herein, means any unsaturated hydrocarbon compound having at least one carbon-to-carbon double bond, i.e., an alkene with a chemical formula of $C_nH_{2n}$. Examples of olefins include ethylene, propylene, butene, and so on.

Accordingly, also disclosed herein is an alkylation process that regenerates a spent ionic liquid catalyst. The alkylation process involves reacting isoparaffins with olefins in the presence of an ionic liquid catalyst comprising a metal halide to provide a spent ionic liquid catalyst comprising conjunct polymer-metal halide complexes and a hydrocarbon product. The alkylation process further involves applying a voltage across one or more pairs of electrodes immersed in the spent ionic liquid catalyst to provide freed conjunct polymers and a regenerated ionic liquid catalyst. After such voltage application, the freed conjunct polymers are separated from the regenerated ionic liquid catalyst and the regenerated ionic liquid catalyst is recycled to the alkylation reaction.

The alkylation process may further include separating the spent ionic liquid catalyst from the hydrocarbon product prior to applying the voltage across the one or more pairs of electrodes immersed in the spent ionic liquid catalyst.

The foregoing discussion regarding the process for regenerating a spent ionic liquid catalyst and the foregoing discussion regarding ionic liquid catalysts also applies to the present alkylation process. For example, the discussion regarding the voltage applied and the length of time that the voltage is applied is also applicable to the present alkylation process. As another example, the discussion regarding chloroaluminate ionic liquid catalysts is similarly applicable to the present alkylation process.

The following examples are provided to further illustrate the present processes and advantages thereof. The examples are meant to be only illustrative, and not limiting.

EXAMPLES

Example 1

Activity of Spent n-Butylpyridinium Heptachlorodialuminate Catalyst

The activities of two different spent n-butylpyridinium heptachlorodialuminate catalysts (Catalyst A and Catalyst B)

were determined by titrating hydrolyzed samples of the catalysts with a dilute potassium hydroxide solution. Catalyst A had an equivalent acid rating of 649 mg KOH/g ionic liquid catalyst. Catalyst B had an equivalent acid rating of 607 mg KOH/g ionic liquid catalyst.

Example 2

Activity of Regenerated n-Butylpyridinium Heptachlorodialuminate Catalyst

Two cylindrical aluminum electrodes (each with a geometric surface area of approximately 2.5 cm² and spaced roughly 1 cm apart) were immersed in 50 cc of spent n-butylpyridinium heptachlorodialuminate catalysts A and B described in Example 1. In each experiment, a third platinum reference electrode was added. This electrode drew no current. Rather, this electrode was connected to a potentiostat to control the potential applied to, what is commonly known in electrochemical literature as, the working electrode. The voltage applied to the working electrode (cathode) was controlled throughout the experiment to a constant value of −0.7 volts relative to the platinum reference electrode. The overall voltage difference between the working and counter (anode) electrodes fluctuated during the timed experiments from 2 to about 3 volts. The current density at the start of each experiment was approximately 6 milliamps per cm². The spent ionic liquids were covered through the electrochemical experiments with 10 cc layers of immiscible toluene. During each of the runs, the solutions were gently stirred with a miniature, magnetic, Teflon® coated stirring bar located at the bottom of the electrochemical cell, several centimeters from the electrode surfaces. At the conclusion of the timed experiments, the electrodes were removed from the solution, and the electrochemically treated ionic liquids were drained from the immiscible toluene top layer.

Samples of these ionic liquids were then hydrolyzed and the hydrolyzed ionic liquid samples were titrated with a dilute potassium hydroxide solution to determine their activities. Table 1 below provides the time periods the voltage was applied to each sample and the corresponding activity (in mg KOH/g ionic liquid catalyst) of each sample.

TABLE 1

| Sample | Time period voltage applied (hours) | Activity (mg KOH/g ionic liquid catalyst) |
| --- | --- | --- |
| Catalyst A | 2 | 694 |
| Catalyst B | 3 | 709 |

Example 3

Activity of Fresh, n-Butylpyridinium Heptachlorodialuminate Catalyst

Titration of a sample of hydrolyzed, fresh n-butylpyridinium heptachlorodialuminate with a dilute potassium hydroxide solution provided an activity of greater than 700 mg KOH/g ionic liquid catalyst. Thus, Examples 1 and 2 illustrate that application of voltage to spent ionic liquid catalyst regenerates the ionic liquid catalyst.

Although the present processes have been described in connection with specific embodiments thereof, it will be appreciated by those skilled in the art that additions, deletions, modifications, and substitutions not specifically described may be made without departing from the spirit and scope of the processes as defined in the appended claims.

That which is claimed is:

1. A process for regenerating a spent ionic liquid catalyst, comprising:
   (a) applying a voltage across one or more pairs of electrodes immersed in a spent ionic liquid catalyst comprising conjunct polymer-metal halide complexes to provide freed conjunct polymers and a regenerated ionic liquid catalyst; and
   (b) separating the freed conjunct polymers from the regenerated ionic liquid catalyst; wherein at least a portion of one or more conjunct polymers of the conjunct polymer-metal halide complexes are electrochemically reduced in step (a) to provide the freed conjunct polymers, halide anions, and the regenerated ionic liquid catalyst.

2. The process according to claim 1, wherein the spent ionic liquid catalyst has been used to catalyze a Friedel-Crafts reaction.

3. The process according to claim 2, wherein the Friedel-Crafts reaction is alkylation.

4. The process according to claim 1, wherein the spent ionic liquid catalyst has been used to catalyze a reaction selected from the group consisting of paraffin alkylation, aromatic alkylation, polymerization, dimerization, oligomerization, acetylation, olefin metathesis, copolymerization, olefin isomerization, desulfurization, catalytic cracking, and combinations thereof.

5. The process according to claim 1, wherein the spent ionic liquid catalyst is a chloroaluminate ionic liquid catalyst.

6. The process according to claim 5, wherein the chloroaluminate ionic liquid catalyst is selected from the group consisting of a pyridinium-based chloroaluminate ionic liquid catalyst, an imidazolium-based chloroaluminate ionic liquid catalyst, and mixtures thereof.

7. The process according to claim 5, wherein the chloroaluminate ionic liquid catalyst is selected from the group consisting of:
   a first chloroaluminate ionic liquid catalyst comprising a hydrocarbyl substituted pyridinium halide of the general formula A and aluminum trichloride or a hydrocarbyl substituted imidazolium halide of the general formula B and aluminum trichloride;
   a second chloroaluminate ionic liquid catalyst comprising an alkyl substituted pyridinium halide of the general formula A and aluminum trichloride or an alkyl substituted imidazolium halide of the general formula B and aluminum trichloride;
   and mixtures thereof,
wherein the general formula A and the general formula B are represented by the structures:

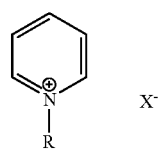

(A)

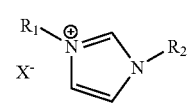

(B)

where R═H, methyl, ethyl, propyl, butyl, pentyl or hexyl group and X is a haloaluminate, and R₁ and R₂═H, methyl, ethyl, propyl, butyl, pentyl, or hexyl group and where $R_1$ and $R_2$ may or may not be the same.

8. The process according to claim 5, wherein the chloroaluminate ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate ($C_5H_5NC_4H_9Al_2Cl_7$), and mixtures thereof.

9. The process according to claim 1, wherein the separation step (b) is selected from the group consisting of decantation, solvent extraction, and combinations thereof.

10. The process according to claim 1, wherein the voltage applied in step (a) is between about 1.5 volts and about 5 volts.

11. The process according to claim 1, wherein the voltage application step (a) further comprises applying a potential to each electrode in each electrode pair that is alternated in time so that each electrode in each electrode pair functions for brief periods of time as a sacrificial anode and for other periods of time as a cathode and further wherein the voltage applied in step (a) is between about 1 volt and about 3 volts.

12. The process according to claim 1, wherein the voltage applied in step (a) provides a current in the spent ionic liquid catalyst having a current density between about 1 and about 200 milliamps/$cm^2$ electrode.

13. The process according to claim 1, wherein the voltage applied in step (a) fluctuates in time to maintain a constant current density in the spent ionic liquid catalyst between about 1 and about 200 milliamps/$cm^2$ electrode.

14. The process according to claim 1, wherein the voltage is applied in step (a) for between about 0.01 hours and about 12 hours.

15. The process according to claim 1, wherein step (a) occurs by applying the voltage across a pair of electrodes immersed in the spent ionic liquid catalyst.

16. A process for regenerating a spent ionic liquid catalyst, comprising:
 (a) applying a voltage across one or more pairs of electrodes immersed in a spent ionic liquid catalyst comprising conjunct polymer-metal halide complexes to provide freed conjunct polymers and a regenerated ionic liquid catalyst; and
 (b) separating the freed conjunct polymers from the regenerated ionic liquid catalyst; wherein a first electrode of each electrode pair is a sacrificial anode composed of aluminum metal and a second electrode of each electrode pair comprises an electrically conducting metal, polymer, or carbon compound.

17. An alkylation process, comprising:
reacting isoparaffins with olefins in the presence of an ionic liquid catalyst comprising a metal halide to provide a spent ionic liquid catalyst comprising conjunct polymer-metal halide complexes and a hydrocarbon product;
applying a voltage across one or more pairs of electrodes immersed in the spent ionic liquid catalyst to provide freed conjunct polymers and a regenerated ionic liquid catalyst;
separating the freed conjunct polymers from the regenerated ionic liquid catalyst; and
recycling the regenerated ionic liquid catalyst to the reacting isoparaffins with olefins; wherein at least a portion of one or more conjunct polymers of the conjunct polymer-metal halide complexes are electrochemically reduced while applying the voltage to provide the freed conjunct polymers, halide anions, and the regenerated ionic liquid catalyst.

18. The process according to claim 17, further comprising separating the spent ionic liquid catalyst from the hydrocarbon product prior to applying the voltage.

19. A process for regenerating a spent ionic liquid catalyst, comprising:
 (a) applying a voltage across one or more pairs of electrodes immersed in a spent ionic liquid catalyst comprising conjunct polymer-metal halide complexes to provide freed conjunct polymers and a regenerated ionic liquid catalyst; wherein the spent ionic liquid catalyst has an immiscible top layer; and
 (b) separating the freed conjunct polymers from the regenerated ionic liquid catalyst); wherein at least a portion of the conjunct polymers of the conjunct polymer-metal halide complexes are electrochemically reduced in step (a) to provide freed conjunct polymers, halide anions, and regenerated ionic liquid catalyst.

20. The process of claim 19, wherein the immiscible top layer comprises toluene.

21. The process of claim 19, additionally comprising draining an electrochemically treated ionic liquid from the immiscible top layer.

22. An alkylation process, comprising:
reacting isoparaffins with olefins in the presence of an ionic liquid catalyst comprising a metal halide to provide a spent ionic liquid catalyst comprising conjunct polymer-metal halide complexes and a hydrocarbon product;
applying a voltage across one or more pairs of electrodes immersed in the spent ionic liquid catalyst to provide freed conjunct polymers and a regenerated ionic liquid catalyst; wherein the spent ionic liquid catalyst has an immiscible top layer;
separating the freed conjunct polymers from the regenerated ionic liquid catalyst; and
recycling the regenerated ionic liquid catalyst to the reacting isoparaffins with olefins; wherein at least a portion of one or more conjunct polymers of the conjunct polymer-metal halide complexes are electrochemically reduced while applying the voltage to provide the freed conjunct polymers, halide anions, and the regenerated ionic liquid catalyst.

23. The alkylation process of claim 22, wherein the immiscible top layer comprises toluene.

24. The alkylation process of claim 22, additionally comprising draining an electrochemically treated ionic liquid from the immiscible top layer.

\* \* \* \* \*